Nov. 1, 1938. M. TANTAU Plant Pat. 300
ROSE PLANT
Filed Jan. 26, 1938
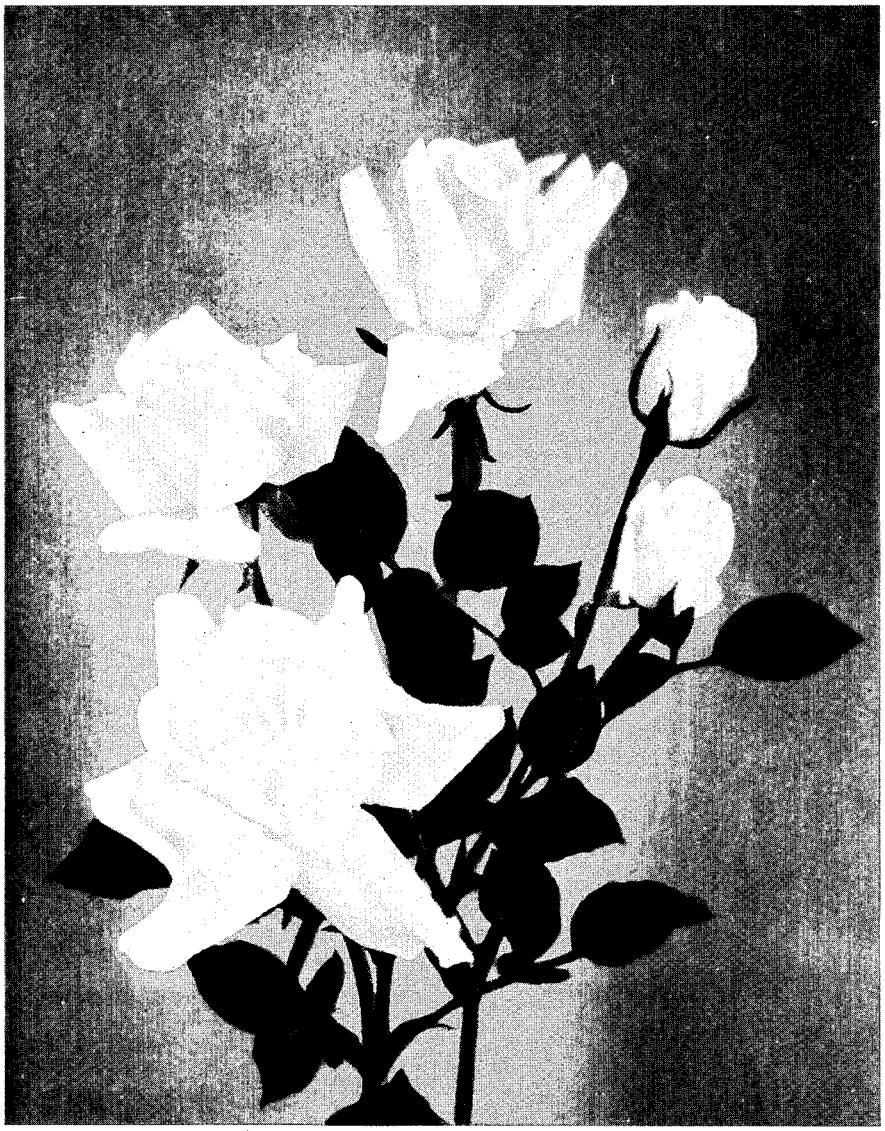
Inventor
Mathias Tantau
By Robb & Robb
attorneys Patented Nov. 1, 1938

UNITED STATES PATENT OFFICE

300

ROSE PLANT

Mathias Tantau, Utersen, Germany, assignor to
The Conard-Pyle Company, West Grove, Pa.

Application January 26, 1938, Serial No. 187,078

1 Claim. (Cl. 47—61)

This invention relates to a new and distinct variety of rose, the result of definite breeding in an effort to produce a rose of a yellow color which has not been known in the particular size and type of flower, to be used for both garden and cut flower purposes.

In order to obtain the foregoing objective, I first crossed the rose Professor Gnau with Julien Potin, and the result of this cross was used as the pollen parent in a cross with Johanna Tantau as the female or seed parent. The result has been to produce what might be called a yellow rose possessing the desirable characteristics of Johanna Tantau, with even more perfect flowers, greater freedom of bloom, and more compactness of growth on the part of the plants.

The new variety is excellently adapted for use as a bedding rose. Its compact habit of growth is particularly suitable for edging, and its uniqueness of golden color, perfectly molded form and profuse blooming habit make it a valuable rose for this purpose.

The star-like effect of the outer petals that curl back in quill-like fashion presents a pleasing appearance, and its long endurance as a cut flower is very desirable for decorative purposes or for boutonniere use.

This new variety has been asexually propagated and is found to reproduce true to form.

The following is a detailed description of this rose plant and its flower, it being understood that there are slight variations from the main characteristics that take place due to environment or season. All color designations are in accordance with Ridgway's Color Standard, except where the ordinary dictionary definition is obviously meant.

Parentage:
- *Seed parent.*—Johanna Tantau.
- *Pollen parent.*—Seedling of Prof. Gnau x Julien Potin.

Classification:
- Polyantha.

*Flower*

Blooming habit:
- Continuous.

Bud:
- *Size.*—Medium.
- *Form.*—Long-pointed petals furl open.
- *Color.*—Light canary to sulphur yellow.
- *Sepals.*—Branched, some are serrated; fold back as bloom opens.
- *Calyx.*—Shallow, goblet-shaped, smooth.
- *Peduncle.*—Short, strong, yellowish green, smooth.
- *Opening.*—Opens perfectly, petals fold back and quill. Never balls.

Bloom:
- *Size.*—3 inches.
- *Borne.*—Singly in branching sprays.
- *Stems.*—Strong.
- *Form.*—Open, with high center. Petals furl to produce quill form and star outline.
- *Permanence.*—Lasts well.
- *Petalage.*—45 to 60 petals.
- *Color.*—Sulphur-yellow.

Petals:
- *Texture.*—Heavy, leathery.
- *Appearance.*—Soft, cushiony.
- *Form.*—Recurve as they open and finally they quill.
- *Arrangement.*—Informal.
- *Persistence.*—Drop off cleanly.
- *Fragrance.*—English primrose.
- *Lasting quality.*—Long.

Genital organs:
- *Stamens, anthers.*—Short, small; color—yellow. Arrangement—regular.
- *Stamens, filaments (threads).*—Uneven; color—light, golden yellow.
- *Styles.*—Bunched.
- *Stigmas.*—Greenish white.
- *Ovaries.*—Normal.

Fruit:
- Variety is sterile with its own pollen.
- *Aspect.*—Smooth.

*Plant*

Form:
- Bush.

Growth:
- Vigorous, very branching.

Foliage:
- Generally five leaflets to compound leaf.
- *Size.*—Medium.
- *Color.*—New foliage—bronzy green; old foliage—olive green.
- *Shape.*—Oval, pointed, undulated.
- *Texture.*—Leathery.
- *Edge.*—Serrated, slightly recurved.
- *Serration.*—Shallow.
- *Ribs and veins.*—Ordinary.
- *Rachis.*—Color—yellowish green; under side—smooth.
- *Stipules.*—Medium, smooth.
- *Disease resistance.*—Resistant to black-spot and mildew.

Thorns:
- *Quantity.*—Very few.
- *Form.*—Scarcely noticeable.

I claim:

A new and distinct variety of rose plant characterized by its compactness of growth, the profuseness of the blossoms, the yellow color thereof not heretofore obtained in the particular size and type of flower, the star-like effect of the outer petals of the flower, and the long endurance of the same as a cut flower, substantially as shown and described.

MATHIAS TANTAU.